United States Patent [19]

Kawada et al.

[11] Patent Number: 5,093,335
[45] Date of Patent: Mar. 3, 1992

[54] DICYANOPYRAZINE COMPOUNDS AND FUNGICIDE

[75] Inventors: Hiroshi Kawada; Katsuya Yamaguchi; Kenichi Tanaka; Yumi Endo, all of Tokyo, Japan

[73] Assignee: Hodogaya Chemical Company, Ltd., Tokyo, Japan

[21] Appl. No.: 469,263

[22] Filed: Jan. 24, 1990

Related U.S. Application Data

[63] Continuation-in-part of Ser. No. 464,393, Jan. 12, 1990, abandoned, which is a continuation of Ser. No. 246,091, Sep. 19, 1988, abandoned.

[30] Foreign Application Priority Data

Sep. 22, 1987 [JP] Japan .................. 62-236210

[51] Int. Cl.$^5$ .................. A01N 43/58; C07D 241/00
[52] U.S. Cl. .................. 514/253; 544/336; 514/255
[58] Field of Search .................. 544/336; 514/253, 255

[56] References Cited

U.S. PATENT DOCUMENTS 4,766,214  8/2388  Cozzi et al. .................. 544/336

Primary Examiner—David B. Springer
Assistant Examiner—Robert C. Whittenbaugh
Attorney, Agent, or Firm—Oblon, Spivak, McClelland, Maier & Neustadt

[57] ABSTRACT

A dicyanopyrazine compound of the formula:

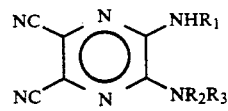

wherein each of $R_1$, $R_2$ and $R_3$ is hydrogen, lower alkyl, lower alkenyl, lower alkynyl, cycloalkyl, aralkyl, substituted aralkyl or thienylmethyl, provided that $R_1$, $R_2$ and $R_3$ are not simultaneously hydrogen and that at least one of $R_1$, $R_2$ and $R_3$ is an alkyl group having four or more carbon atoms.

4 Claims, No Drawings

DICYANOPYRAZINE COMPOUNDS AND FUNGICIDE

The present invention is a continuation-in-part of Ser. No. 07/464,393, filed on 1/12/90 now abandoned. Ser. No. 07/246,091, the later of which was filed on Sept. 19, 1988 now abandoned.

BACKGROUND OF THE INVENTION

1. Field of the Invention

The present invention relates to novel compounds useful as agricultural or horticultural fungicides, a process for their preparation and fungicides containing the same.

2. Description of the Background

Modern agriculture enjoys high productivity depending upon fertilizers, agricultural chemicals and various agricultural tools and materials. On the other hand, there have been serious problems such that resistant microorganisms have been created by continuous use of agricultural chemicals, and plant diseases have been created by continual cultivation of the same crop plants. Under these circumstances, it is strongly desired to develop new and highly safe agricultural chemicals. The present invention provides a means for solving such problems. The present invention provides a dicyanopyrazine compound of the formula:

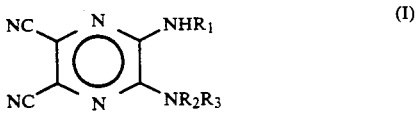

wherein each of $R_1$, $R_2$ and $R_3$ is hydrogen, lower alkyl, lower alkenyl, lower alkynyl, cycloalkyl, aralkyl, substituted aralkyl or thienylmethyl, provided that $R_1$, $R_2$ and $R_3$ are not simultaneously hydrogen and that at one of $R_1$, $R_2$ and $R_3$ is an alkyl group having four or more carbon atoms. The present invention also provides a process for preparing a compound of the formula I which comprises reacting a compound of the formula:

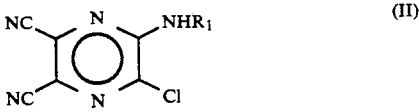

wherein $R_1$ is as defined above, with a compound of the formula:

wherein $R_2$ and $R_3$ are as defined above.

Further, the present invention provides an agricultural or horticultural fungicide which comprises an effective amount of the compound of the formula I as defined above and a carrier or diluent.

Now, the present invention will be described in detail with reference to the preferred embodiments.

Among the compounds of the formula I, particularly preferred are those wherein $R_1$ is hydrogen, $C_1$–$C_5$ alkyl, propenyl or propynyl; $R_2$ is $C_4$–$C_5$ alkyl, $C_3$–$C_5$ alkynyl, $C_5$–$C_7$ cycloalkyl, benzyl, chlorobenzyl, methylbenzyl,

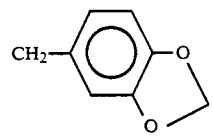

or thienylmethyl;
and $R_3$ is hydrogen or $C_1$–$C_4$ alkyl.

The diamino dicyanopyrazine compounds of the present invention can readily be prepared as shown by the following reaction scheme:

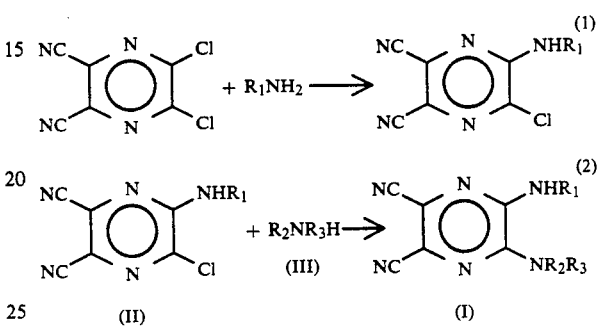

In the above formulas, each of $R_1$, $R_2$ and $R_3$ is hydrogen, lower alkyl, lower alkenyl, lower alkynyl, cycloalkyl, aralkyl, substituted aralkyl or thienylmethyl.

The 2-chloro-3-substituted amino-5,6-dicyanopyrazine obtained by the process of the formula (1) includes known compounds (vide U.S. Pat. Nos. 3,879,394 and 4,054,655). From such dicyanopyrazine, the compound of the formula I of the present invention can be obtained by the process of the formula (2).

This reaction is preferably conducted in an ether solvent such as tetrahydrofuran, dioxane or diethyl ether or in a polar solvent such as N,N-dimethylformamide or dimethylsulfoxide. Such solvents may be used alone or in combination as a mixture.

The reaction temperature is usually within a range of from 0° to 150° C., preferably from room temperature to 60° C. Suitable reaction conditions may easily be selected by those skilled in the art.

When the compounds of the present invention are to be used as fungicides, they may be combined with various carriers in accordance with common techniques for the preparation of agricultural drug formulations and may be used in the form of various formulations such as a wettable powder, an emulsifiable concentrate, a dust, a granule or a dispersion.

Among carriers, liquid carriers may be the usual organic solvents, and solid carriers may be the usual clay minerals, pumice, etc. Further, a surfactant may be added to impart emulsifability, dispersibility or spreadability to the formulation. Further, it may be used in combination with a fertilizer or other agricultural chemicals such as insecticides or other fungicides.

When used as a fungicide, the active compound must be applied in a sufficient amount so that the desired effects can be obtained. The dose is usually within a range of from 50 to 2,000 g/ha, preferably from 200 to 1,000 g/ha. The compound of the present invention is used usually in the form of a formulation such as a wettable powder, an emulsifiable concentrate, a dust, a granule or a dispersion, containing from 0.1 to 50% of the active ingredient.

To prepare an emulsifiable concentrate, the active ingredient is dissolved in an agriculturally acceptable organic solvent, and a solvent-soluble emulsifier is added thereto. As a suitable solvent, xylene, o-chlorotoluene, cyclohexanone, isophorone, dimethylformamide, dimethylsulfoxide or a mixture thereof may be mentioned. Particularly preferred is a solvent mixture comprising an aromatic hydrocarbon or an aromatic hydrocarbon and a ketone and a polar solvent.

The surfactant used as an emulsifier usually constitutes from 1 to 20% by weight of the emulsifiable concentrate and may be cationic, anionic or non-ionic.

Anionic surfactants include alkyl sulfates, alkyl diphenylether disulfonates, naphthylmethane sulfonates, lignin sulfonates, alkylsulfo succinates, alkyl benzene sulfonates and alkyl phosphates. Cationic surfactants include alkylamines and quaternary ammonium salts. Non-ionic surfactants include polyoxyethylene alkyl ethers, polyoxyethylene alkyl aryl ethers, sorbitan fatty acid esters, polyoxyethylene sorbitan fatty acid esters, polyoxyethylene sorbitol fatty acid esters, glycerol fatty acid esters and polyoxyethylene fatty acid esters.

The concentration of the active ingredient is usually within a range of from 0.5 to 20% by weight, preferably form 1 to 10% by weight.

The wettable powder is formulated by adding an active ingredient to a finely pulverized inert solid carrier and a surfactant. The active ingredient is incorporated usually within a range of from 2 to 50% by weight and the surfactant is incorporated usually within a range of from 1 to 20% by weight.

The solid carrier commonly used for the combination with the active ingredient includes a naturally produced clay, a silicate, silica and an alkaline earth metal carbonate. Typical examples include kaolin, zeaklite, talc, diatomaceous earth, magnesium carbonate, calcium carbonate and dolomite.

As commonly employed emulsifiers, extenders, or dispersants, anionic surfactants, non-ionic surfactants or mixtures thereof may be employed. Those similar to the surfactants mentioned above for use for an emulsifiable concentrate may be employed.

The dust formulation is prepared by mixing the active ingredient with an inert carrier commonly employed for the preparation of dust formulations, such as talc, finely pulverized clay, pyrophyllite, diatomaceous earth or magnesium carbonate.

The concentration of the active ingredient is usually within a range of from 0.1 to 20% by weight, preferably from 0.5 to 5% by weight.

The granule formulation is prepared by mixing the active ingredient with a finely pulverized inert carrier such as bentonite, kaoline clay, diatomaceous earth or talc, kneading the mixture with water and then granulating it by a granulating machine. Otherwise, the granule formulation may be prepared by impregnating the active ingredient dissolved together with an extender to a granular carrier preliminarily granulated to have a particle size within a range of from 15 to 30 mesh or to a granular mineral prepared by pulverizing natural pumice, acid clay or zeolite and adjusting the particle size range. The active ingredient in such a granule formulation is usually within a range of from 0.2 to 20% by weight, preferably from 1 to 10% by weight.

The dispersion is prepared by finely pulverizing the active ingredient and mixing it with a surfactant and water. As the surfactant to be used, the anionic surfactants, cationic surfactants and non-ionic surfactants mentioned above for use in an emulsifiable concentrate may by used alone or in combination. The amount of use is usually within a range of from 1 to 20% by weight.

The active ingredient is usually within a range of from 1 to 50% by weight, preferably from 2 to 20% by weight.

Now, the present invention will be described in further detail with reference to examples. However, it should be understood these examples are provided for purposes of illustration and the present invention is by no means restricted by such specific examples.

PREPARATION EXAMPLE 1

Preparation of
2-amino-3-cyclopentyl-5,6-dicyanopyrazine
(Compound No. 19)

(1) Preparation of 2-amino-3-chloro-5,6-dicyanopyrazine 5.0 g (0.025 mol) of 2,3-dichloro-5,6-dicyanopyrazine was dissolved in 50 ml of dry tetrahydrofuran, and 6.1 g (0.050 mol) of 28% aqueous ammonia was dropwise added at a temperature of from $-15°$ to $0°$ C. After completion of the dropwise addition, the mixture was stirred for 1 hour, and the reaction solution was poured into 500 ml of water. The precipitated solid was collected by filtration and recrystallized from a solvent mixture of toluene and ethyl acetate to obtain 4.2 g of slightly yellow crystals (yield: 93.6%, melting point: 205–208° C.).

(2) Preparation of 2-amino-3-cyclopentylamino-5,6-dicyanopyrazine 4.2 g (0.023 mol) of 2-amino-3-chloro-5,6-dicyanopyrazine was dissolved in 50 ml of dry tetrahydrofuran, and 4.0 g (0.047 mol) of cyclopentylamine was dropwise added thereto at room temperature. After completion of the dropwise addition, the mixture was stirred at 40° C. for 1 hour, and the reaction solution was poured into 500 ml of water. The precipitated solid was collected by filtration and recrystallized from isobutyl alcohol to obtain 4.9 g of slightly yellow crystals (yield: 93.4%, decomposition point: 222° C.).

PREPARATION EXAMPLE 2

Preparation of
2-amino-3-tert-butylamino-5,6-dicyanopyrazine
(Compound No. 9)

(1) Preparation of 2-chloro-3-tert-butylamino-5,6-dicyanopyrazine 5.0 g (0.025 mol) of 2,3-dichloro-5,6-dicyanopyrazine was dissolved in 50 ml of dry tetrahydrofuran, and 25 ml of a dry tetrahydrofuran solution containing 3.7 g (0.050 mol) of tert-butylamine was dropwise added thereto at a temperature of from $-15°$ to $0°$ C. After completion of the dropwise addition, the mixture was stirred for 2 hours, and the reaction solution was poured into 500 ml of water. The precipitated solid was collected by filtration and recrystallized from toluene to obtain 4.5 g of slightly yellow crystals (yield: 76.4%, melting point: 174°–176° C.).

(2) Preparation of 2-amino-3-tert-butylamino-5,6-dicyanopyrazine 2.0 g (0.008 mol) of 2-chloro-3-tert-butylamino-5,6-dicyanopyrazine was dissolved in 100 ml of dry N,N-dimethylformamide, and ammonia gas was blown into it under stirring at room temperature. Two hours later, the reaction solution was poured into 1 liter of water and neutralized with hydrochloric acid. The precipitated solid was collected by filtration and recrystallized from isobutyl alcohol to obtain 1.2 g of slightly yellow crystals (yield: 69.4%, melting point: at least 250° C.).

PREPARATION EXAMPLE 3

Preparation of 2-methylamino-3-tert-butylamino-5,6-dicyanopyrazine (Compound No. 27)

2.0 g (0.008 mol) of 2-chloro-3-tert-butylamino-5,6-dicyanopyrazine was dissolved in 50 ml of tetrahydrofuran., and 1.3 g (0.017 mol) of a 40% methylamine aqueous solution was dropwise added thereto at room temperature. The mixture was stirred for 1 hour, and then the reaction solution was poured into 500 ml of water. The precipitated solid was collected by filtration and recrystallized from isobutyl alcohol to obtain 1.4 g of slightly yellow crystals (yield: 76.1%, melting point: at least 250° C.).

Now, representative compounds of the present invention are shown in Table 1.

TABLE 1

Compounds of the formula:

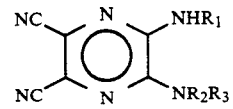

| Compound No. | $R_1$ | $R_2$ | $R_3$ | M.P. (°C.) | IR spectrum (cm$^{-1}$) |
|---|---|---|---|---|---|
| 5 | H | $CH_2C{\equiv}CH$ | H | 235(dec.) | 3420, 3350, 3250, 3150, 2240, 1670, 1570 |
| 6 | H | $CH_2(CH_2)_2CH_3$ | H | >250 | 3400, 3320, 3150, 2220, 1660, 1580 |
| 7 | H | $CH_2CH(CH_3)_2$ | H | 205(dec.) | 3420, 3380, 3310, 3130, 2210, 1655, 1575 |
| 8 | H | $CH(CH_3)CH_2CH_3$ | H | 215(dec.) | 3470, 3440, 3375, 3320, 3240, 2230, 1640, 1570 |
| 9 | H | $C(CH_3)_3$ | H | >250 | 3410, 3370, 3310, 3210, 3160, 2230, 1660, 1565 |
| 10 | H | $C(CH_3)_2C{\equiv}CH$ | H | 202(dec.) | 3440, 3370, 3340, 3270, 3230, 2230, 1635, 1565 |
| 11 | H | $CH_2(CH_2)_3CH_3$ | H | 187(dec.) | 3400, 3320, 3150, 2210, 1660, 1575 |
| 12 | H | $CH_2CH_2CH(CH_3)_2$ | H | 214(dec.) | 3410, 3325, 3170, 2225, 1665, 1580 |
| 13 | H | $CH_2C(CH_3)_3$ | H | 228–230 | 3460, 3360, 3330, 3230, 2220, 1635, 1575 |
| 14 | H | $C(CH_3)_2CH_2CH_3$ | H | 201–203 | 3390, 3320, 3160 2230, 1660, 1570 |
| 15 | H | $CH(CH_3)(CH_2)_2CH_3$ | H | 192–195 | 3470, 3410, 3370, 3240, 3150, 2220, 1650, 1630, 1570 |
| 16 | H | $CH_2CH(CH_3)CH_2CH_3$ | H | 196(dec.) | 3380, 3320, 3150, 2220, 1660, 1570 |
| 17 | H | $CH(CH_2CH_3)_2$ | H | 197–200 | 3450, 3420, 3330, 3320, 3150, 2230, 1675, 1640, 1570 |
| 18 | H | $CH(CH_3)CH(CH_3)_2$ | H | 214(dec.) | 3470, 3440, 3380, 3350, 3310, 3230, 2230, 1645, 1570 |
| 19 | H | cyclo-$C_5H_9$ | H | 222(dec.) | 3440, 3410, 3360, 3310, 3230, 3160, 2230, 1645, 1580 |
| 20 | H | $CH_2(CH_2)_4CH_3$ | H | 184–188 | 3400, 3325, 3150, 2230, 2220, 1660, 1580 |
| 21 | H | $CH_2CH(CH_2CH_3)_2$ | H | 169–171 | 3400, 3330, 3150, 2220, 1660, 1575 |
| 22 | H | $CH_2CH_2C(CH_3)_3$ | H | 153–157 | 3410, 3320, 3150, 2220, 1660, 1575 |
| 23 | H | $CH(CH_3)CH_2CH(CH_3)_2$ | H | 212(dec.) | 3455, 3400, 3360, 3230, 3150, 2220, 1660, 1635, 1570 |
| 24 | H | $CH_1CH_3C(CH_3)_3$ | H | 235(dec.) | 3410, 3330, 3180, 2240, 1660, 1570 |
| 25 | H | cyclo-$C_6H_{11}$ | H | >250 | 3475, 3440, 3380, 3350, 3230, 2240, 1630, 1585 |
| 26 | H | $CH_2(CH_2)_5CH_3$ | H | 173(dec.) | 3400, 3320, 3160, 2220, 1660, 1580 |
| 27 | $CH_3$ | $C(CH_3)_3$ | H | >250 | 3400, 3375, 2220, 1590 |
| 28 | $CH_3$ | $CH_2CH_2CH(CH_3)_2$ | H | 188–190 | 3390, 2225, 1590 |

TABLE 1-continued

Compounds of the formula:

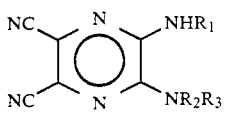

| Compound No. | R₁ | R₂ | R₃ | M.P. (°C.) | IR spectrum (cm⁻¹) |
|---|---|---|---|---|---|
| 29 | $CH_3$ | cyclo-$C_5H_9$ | H | >250 | 3380, 3360, 2220, 1590, 1555 |
| 30 | $CH_2C{\equiv}CH$ | cyclo-$C_5H_9$ | H | 197–199 | 3370, 3260, 2220, 1580, 1540 |
| 32 | $C(CH_3)_3$ | $C(CH_3)_3$ | H | 224(dec.) | 3380, 3320, 2230, 1585 |
| 33 | $CH_2(CH_2)_3CH_3$ | $CH_2(CH_2)_3CH_3$ | H | 126–129 | 3380, 2220, 1580, 1560 |
| 34 | H | $CH_2$–C₆H₅ | H | 183(dec.) | 3460, 3380, 3350, 2230, 1630, 1575 |
| 35 | H | $CH_2$–C₆H₄–Cl | H | 199(dec.) | 3390, 3130, 2220, 1650, 1565 |
| 36 | H | $CH_2$–(methylenedioxyphenyl) | H | 232(dec.) | 3440, 3370, 3330, 3240, 2230, 1640, 1580, 1100 |
| 37 | H | $CH_2$–(2-thienyl) | H | 177(dec.) | 3480, 3360, 3150, 2230, 1660, 1630, 1580 |
| 38 | $CH_2CH_3$ | cyclo-$C_5H_9$ | H | 202–204 | 3390, 2230, 1590, 1550 |
| 39 | $CH_2CH_2CH_3$ | cyclo-$C_5H_9$ | H | 238–239.5 | 3400, 2220, 1590, 1550 |
| 40 | $CH(CH_3)_2$ | cyclo-$C_5H_9$ | H | 222–223 | 3395, 3350, 2230, 1590, 1550 |
| 41 | $CH_2CH{=}CH_2$ | cyclo-$C_5H_9$ | H | 173–175 | 3390, 2225, 1590, 1550 |
| 42 | $CH_2CH(CH_3)_2$ | cyclo-$C_5H_9$ | H | 200–201 | 3390, 2220, 1590, 1550 |
| 43 | $C(CH_3)_3$ | cyclo-$C_5H_9$ | H | 228–230 | 3390, 2230, 1590, 1550 |
| 44 | H | $CH_2$–C₆H₄–$CH_3$ | H | >250 | 3470, 3410, 3350, 2230, 1675, 1635, 1580 |
| 45 | cyclo-$C_6H_{11}$ | $CH_2CH_3$ | $CH_2CH_3$ | 80.5–82 | 3330, 2230, 1560, 1530 |
| 46 | H | $CH_2CH_3(CH_3)_2$ | $CH_3$ | 109.5–110 | 3475, 3290, 3180, 2230, 1635, 1550 |
| 47 | H | endo-bicyclo[2,2,1]heptan-2-yl | H | 227 | 3460, 3320, 3150, 2230, 1650, 1575 |
| 48 | H | exo-bicyclo[2,2,1]heptan-2-yl | H | 235 | 3460, 3330, 3140, 2230, 1650, 1575 |

FORMULATION EXAMPLE 1

Emulsifiable concentrate

| | By weight |
|---|---|
| Compound No. 30 | 2 parts |
| o-Chlorotoluene | 50 parts |
| Cyclohexanone | 38 parts |
| N-methylpyrrolidone | 5 parts |
| Sorpol 800A (trademark, Toho Chemical | 5 parts |

-continued

|  | By weight |
|---|---|
| Company) |  |

The above components are uniformly mixed and dissolved to obtain an emulsifiable concentrate of the present invention.

FORMULATION EXAMPLE 2

Wettable powder

|  | By weight |
|---|---|
| Compound No. 7 | 15 parts |
| Kaolin clay | 78 parts |
| Sorpol 5039 | 5 parts |
| Sorpol 5060 | 1 part |
| Vannox powder (trademark, Nippon Nyukazai K.K.) | 1 part |

The above components were mixed and pulverized to obtain a wettable powder of the present invention.

FORMULATION EXAMPLE 3

Dust

|  | By weight |
|---|---|
| Compound No. 16 | 2 parts |
| Kaolin clay | 98 parts |

The above components were mixed and pulverized to obtain a dust of the present invention.

FORMULATION EXAMPLE 4

Granule

|  | By weight |
|---|---|
| Compound No. 19 | 5 parts |
| Bentonite | 45 parts |
| Talc | 45 parts |
| Sodium lignin sulfonate | 5 parts |

The above components were uniformly mixed and pulverized, and then kneaded by the addition of water. The mixture was granulated and dried to obtain a granule formulation of the present invention.

FORMULATION EXAMPLE 5

Dispersion

|  | By weight |
|---|---|
| Compound No. 34 | 10 parts |
| Ethylene glycol | 5 parts |
| Sorpol 3078 | 5 parts |
| Sorpol 7512 | 0.5 part |
| Water | 79.5 parts |

The above components were uniformly mixed and pulverized to obtain a disperion formulation of the present invention.

FORMULATION EXAMPLE 6

Wettable powder

|  | By weight |
|---|---|
| Compound No. 13 | 10 parts |
| Kaolin clay | 79.5 parts |
| Sorpol 5039 | 7 parts |
| Sodium bisnaphthalene sulfonate | 3.5 parts |

The above components were mixed and pulverized to obtain a wettable powder of the present invention.

FORMULATION EXAMPLE 7

Wettable powder

|  | By weight |
|---|---|
| Compound No. 19 | 35 parts |
| Kaolin clay | 49 parts |
| Sorpol 5060 | 6 parts |
| Sorpol 5039 | 6 parts |
| Sodium bisnaphthalene sulfonate | 4 parts |

The above components were mixed and pulverized to obtain a wettable powder of the present invention.

FORMULATION EXAMPLE 8

Wettable powder

|  | By weight |
|---|---|
| Compound No. 38 | 85 parts |
| Sorpol 5039 | 10 parts |
| Sodium bisnaphthalene sulfonate | 5 parts |

The above components were mixed and pulverized to obtain a wettable powder of the present invention.

FORMULATION EXAMPLE 9

Wettable powder

|  | By weight |
|---|---|
| Compound No. 44 | 10 parts |
| Kaolin clay | 78 parts |
| Sorpol 5039 | 6 parts |
| Surfinol 440 (trademark, Nisshin Kagaku Kogyo K.K.) | 1 part |
| Vannox powder | 5 parts |

The above components were mixed and pulverized to obtain a wettable powder of the present invention.

Now, the fungicidal effects and disease-preventing effects of the fungicides of the present invention against typical fungi will be described with reference to test examples.

TEST EXAMPLE 1

Direct fungicidal activities on a Petri dish

In a Petri dish having a diameter of 9 cm, an agar plate was prepared by mixing a dimethyl sulfoxide solution of the compound and a potato dextrose agar culture medium (PDA culture medium) (or a vegetable juice agar culture medium in the case of Phytophthora, the same applies hereinafter) to obtain a predetermined concentration. On this agar plate, two mycelia discs of 4 mm in diameter punched out from a mass of mycelia propagated preliminarily on a PDA culture medium were placed and cultured at 25° C. for three days in the case of *Pythium graminicola,* for five days in the case of *Fusarium oxysporum,* or for three days in the case of *Rhizoctonia solani,* whereupon colony diameters were measured in comparison with the colony diameters where no fungicide was added and the growth inhibition rate was calculated. The average of the results is shown in Table 2.

healthy seedlings was counted. The test was conducted in duplicate. The results are shown in Table 3.

TABLE 3

| Compound No. | Proportion of healthy seedlings (%) | Compound No. | Proportion of healthy seedlings (%) |
|---|---|---|---|
| 6 | 63 | 16 | 85 |
| 7 | 88 | 19 | 98 |
| 8 | 71 | 21 | 68 |

TABLE 2

| | Type of fungus | | | | | | | | | |
|---|---|---|---|---|---|---|---|---|---|---|
| | Phytophthora | | | Pythium | | | | Fusarium | | Rhizoctonia | |
| Concentration (ppm) | 50 | 10 | 5 | 100 | 10 | 5 | 2.5 | 100 | 10 | 100 | 10 |
| Compound No. | | | | | | | | | | | |
| 5 | — | — | — | 95 | 4 | — | — | — | — | 35 | — |
| 6 | — | — | — | 100 | 73 | — | — | 31 | 38 | 31 | — |
| 7 | 86 | 66 | 49 | 100 | 100 | 100 | 56 | 47 | — | 46 | — |
| 8 | — | — | — | 100 | 100 | 45 | 22 | 65 | — | 63 | — |
| 9 | 80 | 39 | 20 | 100 | 100 | 44 | 17 | 48 | — | 36 | — |
| 10 | — | — | — | 85 | 29 | — | — | 36 | — | 40 | — |
| 11 | 75 | 72 | 55 | 100 | 100 | 95 | 55 | 18 | 30 | 28 | 12 |
| 12 | 79 | 74 | 62 | 100 | 100 | 100 | 56 | 47 | — | 46 | — |
| 13 | 98 | 83 | 76 | 100 | 100 | 100 | 100 | 42 | — | 23 | — |
| 14 | — | — | — | 100 | 83 | 71 | 43 | 90 | | 100 | 81 |
| 15 | — | — | — | 100 | 95 | 68 | 32 | 67 | — | 82 | — |
| 16 | — | — | — | 100 | 100 | 80 | 49 | 51 | — | 51 | — |
| 17 | — | — | — | 100 | 98 | 70 | 6 | 70 | | 78 | |
| 18 | — | — | — | 100 | 100 | 100 | 50 | 70 | — | 92 | — |
| 19 | — | — | — | 100 | 100 | 100 | 100 | 58 | — | 49 | — |
| 20 | — | — | — | 67 | 75 | — | — | 29 | 21 | 39 | 8 |
| 21 | 68 | 58 | 37 | 98 | 98 | 96 | 48 | 46 | — | 68 | — |
| 22 | 64 | 62 | 45 | 100 | 100 | 83 | 59 | 29 | — | 36 | 29 |
| 23 | 81 | 63 | 39 | 100 | 89 | 83 | 47 | 78 | — | 98 | — |
| 24 | — | — | — | 100 | 98 | 86 | 72 | 69 | — | 85 | — |
| 25 | 84 | 76 | 47 | 100 | 98 | 85 | 65 | 44 | — | 50 | — |
| 26 | — | — | — | 69 | 3 | — | — | 21 | — | 40 | — |
| 27 | — | — | — | 100 | 51 | — | — | 39 | — | 53 | — |
| 28 | — | — | — | 100 | 98 | — | — | 44 | — | 50 | — |
| 29 | — | — | — | 100 | 100 | 80 | 53 | 40 | — | 51 | — |
| 30 | — | — | — | 95 | 95 | — | — | 55 | — | 40 | — |
| 32 | — | — | — | 100 | 10 | — | — | 88 | 62 | 100 | 99 |
| 33 | — | — | — | 12 | 15 | — | — | 33 | 33 | 38 | 27 |
| 34 | 85 | 42 | 27 | 100 | 100 | 43 | 12 | 42 | — | 57 | — |
| 35 | — | — | — | 95 | 91 | 83 | 77 | 31 | — | 36 | — |
| 36 | — | — | — | 100 | 98 | 90 | 62 | 28 | — | 27 | — |
| 37 | — | — | — | 100 | 100 | 75 | 30 | 56 | — | 62 | — |
| 38 | — | — | — | — | 95 | 83 | 68 | — | — | — | — |
| 39 | — | — | — | — | 66 | 65 | 68 | — | — | — | — |
| 40 | — | — | — | — | 63 | 64 | 65 | — | — | — | — |
| 41 | — | — | — | — | 95 | 95 | 72 | — | — | — | — |
| 42 | — | — | — | — | 66 | 64 | 58 | — | — | — | — |
| 43 | — | — | — | 46 | 22 | — | — | — | — | — | — |
| 44 | — | — | — | — | 100 | 95 | 68 | — | — | — | — |
| 45 | — | — | — | 100 | 48 | — | — | 47 | — | 78 | — |
| 46 | — | — | — | — | 80 | 56 | 35 | — | — | — | — |
| 47 | — | — | — | 100 | 100 | 100 | 100 | 26 | — | 14 | — |
| 48 | — | — | — | 100 | 100 | 100 | 100 | 53 | — | 44 | — |

TEST EXAMPLE 2

Control of pythium graminicola 500 ml of air-dried paddy field soil and a dust of a compound formulated in accordance with Formulation Example 3 to have an active ingredient concentration of 10 ppm were mixed and filled in a resin container having a depth of 7 cm and an area of 150 cm². 50 seeds of paddy rice (variety: Koshihikari) were sown, inoculated with homogenized mycelia of *Pythium gaminicola* and irrigated with water. The container was kept at a temperature of from 20° to 25° C. and after one main leaf opened, the container was kept at 5° C. for 4 days. Then, the container was returned to a temperature of from 20° to 25° C., and 5 days later, the number of

| | | | |
|---|---|---|---|
| 10 | 81 | 25 | 94 |
| 11 | 88 | 26 | 73 |
| 12 | 90 | 30 | 96 |
| 13 | 93 | 34 | 84 |
| 14 | 76 | No treatment | 34 |

TEST EXAMPLE 3

Control of the damping-off of rice caused by *Rhizopus chinensis*

100 ml of air-dried paddy field soil and an emulsifiable concentrate of a compound formulated in accordance with Formulation Example 1 to have an active ingredient concentration of 30 ppm were mixed and filled in a resin container having a depth of 8 cm and an area of 50 cm². 100 seeds of paddy rice (variety: Koshihikari) were sown, inoculated with a dispersion of spores of *Rhizopus chinensis* and irrigated with water. A transparent plastic cover was put on the container, and the container was kept at 30° C. When two main leaves opened, the roots were dug up, whereupon the presence or absence of an abnormality of roots due to toxin of *Rhizopus chinensis* was examined to determine the effectiveness. The test was conducted in duplicate. The results are shown in Table 4.

TABLE 4

| Compound No. | Proportion of healthy seedlings (%) | Compound No. | Proportion of healthy seedlings (%) |
|---|---|---|---|
| 7 | 67.5 | 17 | 72.0 |
| 12 | 48.5 | 19 | 7.5 |
| 13 | 4.5 | 25 | 60.5 |
| 14 | 30.0 | 30 | 57.5 |
| 16 | 72.0 | No treatment | 8.0 |

TEST EXAMPLE 4

Control of the damping-off of rice seedlings caused by *Fusarium roreum*

100 ml of air-dried paddy field soil and an emulsifiable concentrate of a compound formulated in accordance with Formulation Example 1 to have an active ingredient concentration of 30 ppm were mixed and filled in a resin container having a depth of 8 cm and an area of 50 cm². 100 seeds of paddy rice (variety: Koshihikari) were sown, inoculated with homogenized mycelia of *Fusarium roreum* and irrigated with water. The container was kept at a temperature of from 20° to 25° C., and after a main leaf opened, the container was kept at 5° C. for 4 days. Thereafter, it was kept at 25° C., and five days later, the number of healthy seedlings was counted. The test was conducted in duplicate. The results are shown in Table 5.

TABLE 5

| Compound No. | Proportion of healthy seedlings (%) | Compound No. | Proportion of healthy seedlings (%) |
|---|---|---|---|
| 7 | 77.5 | 19 | 68.5 |
| 14 | 32.0 | 30 | 96.0 |
| 16 | 93.0 | No treatment | 22.5 |

TEST EXAMPLE 5

Improvement in the proportion of healthy seedlings by direct seeding cultivation in irrigated paddy field soil In the middle of May, seeds of paddy rice powder-coated with calcium peroxide were sown in puddled and leveled paddy field soil at a depth of about 10 mm. Variety: Koshihikari, amount of seeding: 4 kg/10a. The paddy field was irrigated to a water depth of about 4 cm, and the fungicide of the present invention prepared in Formulation Example 4 was applied in an amount corresponding to 6 kg/10a. In the middle of June when about four main leaves opened, the proportion of healthy seedlings was investigated. The experiment was conducted with a unit area of 6 m² in duplicate. The experiment was conducted at two separate sites. The results are shown in Table 6.

TABLE 6

| Fungicide | Proportion of healthy seedlings (%) | |
|---|---|---|
| | Site A | Site B |
| Fungicide of the present invention | 80.4 | 66.4 |
| No treatment | 56.8 | 54.0 |

TEST EXAMPLE 6

Prevention of cucumber disease

Cucumber (variety: Kashu 1 gou) was cultivated in a porous pot having a diameter of 9 cm. When it reached a 3-leaf stage, a compound formulated in accordance with Formulation Example 6 was adjusted to 100 ppm, and 10 ml of the dispersion of the compound was applied by a spray gun. Three plants were treated by each test compound. After drying for 4 hours, a suspension of spores ($2 \times 10^5$ spores/ml) of *Phytophthora capsici* which causes the cucumber disease was spray-inoculated to the plants. After the inoculation, the cucumber plants were cultured at 27° C. under a moisture saturated condition for 24 hours and then cultured at 27° C. under a relative humidity of from 70 to 80% for two days. Three days after the inoculation, diseased spots on the first leaf and the second leaf were examined, and the control value was determined as shown below to obtain the results as shown in Table 7.

$$\text{Control value (\%)} = \frac{A - B}{A} \times 100$$

where A is the proportion of diseased spots in the non-treated seedlings, and B is the proportion of diseased spots in the treated seedlings.

TABLE 7

| Compound No. | Control value (%) |
|---|---|
| 7 | 64 |
| 13 | 85 |
| 19 | 83 |
| 24 | 55 |
| 25 | 65 |
| 29 | 60 |
| 30 | 70 |
| 35 | 65 |
| 40 | 62 |
| 41 | 70 |

TEST EXAMPLE 7

Prevention of cucumber downy mildew

Cucumber (variety: Kashu 1 gou) was cultivated in a porous pot having a diameter of 9 cm. When it reached a 3-leaf stage, each test compound formulated in accordance with Formulation Example 6 was adjusted to 100 ppm, and 10 ml of the dispersion of the test compound was applied by a spray gun. Three plants were treated by each test compound.

After drying for 4 hours, a suspension of spores ($2 \times 10^5$ spores/ml) of *Pseudoperonospora cubensis* which causes cucumber downy mildew was spray-inoculated to the plants. The inoculated cucumber plants were cultured at 20° C. under a moisture saturated condition for 24 hours and then cultured 20° C. under a relative humidity of from 70 to 80% for 6 days. Seven days after the inoculation, the proportion of diseased spots on the first leaf and the second leaf was examined, and the control value was obtained in the same manner as in Test Example 6. The results are shown in Table 8.

TABLE 8

| Compound No. | Control value (%) |
|---|---|
| 13 | 90 |
| 19 | 87 |
| 29 | 50 |
| 30 | 65 |
| 40 | 70 |
| 41 | 75 |

Additionally, the following comparative experiments have also been conducted.

COMPARATIVE EXPERIMENT I

Test Example 6 of the present specification was repeated by using the following compounds, the results of which are summarized in the following table.

| | | Compound No. | Control Value (%) | $R_1$ | $R_2$ | $R_3$ |
|---|---|---|---|---|---|---|
| A* | Within the Scope of the present invention | 7 | 64 | H | $CH_2CH(CH_3)_2$ | H |
| B* | Within the Scope of the present invention | 13 | 85 | H | $CH_2C(CH_3)_3$ | H |
| C | Outside of the Scope of the present invention | 2 | 21 | H | $CH_2CH_3$ | H |
| D | Outside of the Scope of the present invention | 4 | 23 | H | $CH(CH_3)_2$ | H |
| E** | Outside of the Scope of the present invention | — | 20 | $CH_2CH_3$ | $CH_2CH_3$ | H |
| F** | Outside of the Scope of the present invention | 31 | 18 | $CH(CH_3)_2$ | $CH(CH_3)_2$ | H |

*Control values are disclosed in the present specification.
**E and F are compounds disclosed in Nakamura et al, Agric. Biol. Chem., 1983, 47(7), p. 1561-7.

COMPARATIVE EXPERIMENT II

Test Example 7 of the present specification was repeated by using the following compounds, the results of which are summarized in the following table.

| | | Compound No. | Control Value (%) | $R_1$ | $R_2$ | $R_3$ |
|---|---|---|---|---|---|---|
| A* | Within the Scope of the present invention | 7 | 65 | H | $CH_2CH(CH_3)_2$ | H |
| B* | Within the Scope of the present invention | 13 | 90 | H | $CH_2C(CH_3)_3$ | H |
| C | Outside of the Scope of the present invention | 2 | 19 | H | $CH_2CH_3$ | H |
| D | Outside of the Scope of the present invention | 4 | 20 | H | $CH(CH_3)_2$ | H |
| E** | Outside of the Scope of the present invention | — | 25 | $CH_2CH_3$ | $CH_2CH_3$ | H |
| F** | Outside of the Scope of the present invention | 31 | 22 | $CH(CH_3)_2$ | $CH(CH_3)_2$ | H |

*Control values are disclosed in the present specification.
**E and F are compounds disclosed in Nakamura et al, Agric. Biol. Chem., 1983, 47(7), p. 1561-7.

As can be seen from the above data, compounds A and B, which are within the scope of the present invention wherein at least one of $R_1$, $R_2$ and $R_3$ is an alkyl group having four or more carbon atoms, are more effective than Compounds C, D, E and F which are outside of the scope of the present invention.

Having described the present invention, it will be apparent to the artisan that many changes and modifica-

We claim:

1. A dicyanopyrazine compound of the formula (I):

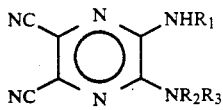

wherein $R_1$ is hydrogen, $C_6$ cycloalkyl, $C_1$-$C_5$ alkyl, propenyl or propynyl; $R_2$ is $C_2$-$C_7$ alkyl, $C_3$-$C_5$ alkynyl, $C_5$-$C_7$ cycloalkyl, benzyl, chlorobenzyl, methylbenzyl,

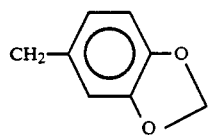

or thienylmethyl; and $R_3$ is hydrogen or $C_1$-$C_4$ alkyl, provided that at least one of $R_1$ and $R_2$ is an alky group having four or more carbon atoms.

2. A fungicide, comprising:
   a) an effective amount of a dicyanopyrazine compound of the formula (I):

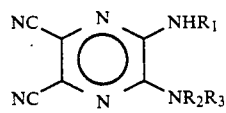

wherein $R_1$ is hydrogen, $C_6$ cycloalkyl, $C_1$-$C_5$ alkyl, propenyl or propynyl; $R_2$ is $C_2$-$C_7$ alkyl, $C_3$-$C_5$ alkynyl, $C_5$-$C_7$ cycloalkyl, benzyl, chlorobenzyl, methylbenzyl,

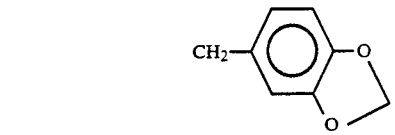

or thienylmethyl; and $R_3$ is hydrogen or $C_1$-$C_4$ alkyl, provided that at least one of $R_1$ and $R_2$ is an alkyl group having four or more carbon atoms;
   b) a carrier or diluent.

3. The fungicide according to claim 2, wherein said dicyanopyrazine compound is contained in the amount of from 0.5 to 20% by weight.

4. The fungicide according to claim 3, wherein said dicyanopyrazine compound is contained in the amount of from 1 to 10% by weight.

* * * * *